United States Patent [19]
Brown et al.

[11] Patent Number: 5,743,868
[45] Date of Patent: Apr. 28, 1998

[54] CORNEAL PRESSURE-REGULATING IMPLANT DEVICE

[76] Inventors: Reay H. Brown; Keith P. Thompson, both of 4375 E. Brookhaven Ave., Atlanta, Ga. 30319

[21] Appl. No.: 195,614

[22] Filed: Feb. 14, 1994

[51] Int. Cl.⁶ .................. A61M 5/00; A61F 2/14
[52] U.S. Cl. ............. 604/8; 604/9; 604/264; 604/294; 623/4; 623/5
[58] Field of Search ............. 623/4, 5; 604/8–10, 604/289, 290, 294, 264

[56] References Cited

U.S. PATENT DOCUMENTS

| | | |
|---|---|---|
| 4,402,681 | 9/1983 | Haas et al. ................ 604/9 |
| 5,092,837 | 3/1992 | Ritch et al. ................ 604/8 |
| 5,127,901 | 7/1992 | Odrich ....................... 604/9 |
| 5,300,020 | 4/1994 | L'Esperance, Jr. ........ 604/9 |
| 5,372,577 | 12/1994 | Ungerleider ............... 604/8 |

*Primary Examiner*—Mary Beth Jones
*Attorney, Agent, or Firm*—James W. Kayden, Esq.; Hopkins & Thomas, L.L.P.

[57] ABSTRACT

A unitary, pressure-regulating corneal implant device for use in controlling intraocular pressure of the cornea is disclosed, the implant having a conduit with a bore and a porous core material disposed in the bore for allowing egress of aqueous humor from the anterior chamber of the eye. The conduit is elongated for extending from the ocular surface of the eye substantially flush therewith through the corneal stroma, and into the anterior chamber.

11 Claims, 1 Drawing Sheet

CORNEAL PRESSURE-REGULATING IMPLANT DEVICE

FIELD OF THE INVENTION

This invention relates to the relief of pathologic elevation of internal eye pressure (glaucoma) using an implanted device. The device provides a conduit means through which ocular fluid drains directly to the ocular surface. This external drainage bypasses the obstructed internal drainage system of the eye. By reducing intraocular pressure, the damage from glaucoma is halted or prevented.

BACKGROUND OF THE INVENTION

The eyeball is a hollow sphere with a semi-rigid outer shell (sclera or "white" portion of the eye) consisting of collagen. A gel material (vitreous humor) fills the posterior two-thirds of the eye. The vitreous humor is sequestered behind the lens and generally does not contribute to ocular pressure. A water-like substance (aqueous humor) fills the space posterior to the cornea and anterior to the lens and iris. The aqueous humor is produced behind the base of the iris and migrates forward into the anterior chamber. It then drains out of the eye through the trabecular meshwork system located between the iris and cornea into channels in the sclera where it is conducted back into the bloodstream.

The internal pressure in the eye is determined by a balance between the production of aqueous humor and the resistance to its outflow. Elevated intraocular pressure is caused by an obstruction in the outflow system. Glaucoma occurs when this elevated pressure causes damage to vision. If not adequately treated, glaucoma eventually causes blindness. The therapy for glaucoma consists of eyedrops, pills, laser treatment, and surgery. Eyedrops and pills are tried first and eyes that fail to respond adequately to these measures receive laser treatment. Glaucomatous eyes that continue to have an elevated pressure despite medical treatments require a surgical procedure.

A conventional operation for glaucoma begins with an incision in the conjunctiva—a very thin tissue layer covering the sclera. This incision is extended down through the subconjunctival connective tissue that lies between the sclera and the conjunctiva. A broad area of sclera is thereby exposed. An opening or fistula is created surgically through the sclera and trabecular meshwork into the anterior chamber of the eye. The incisions in the subconjunctival tissue and conjunctiva are closed with sutures while the scleral fistula is left open. If the operation is successful, the intraocular pressure is reduced by fluid flowing through the scleral hole and percolating slowly through the intact conjunctiva covering the hole.

The success of a glaucoma operation depends on the scleral fistula remaining patent and the absence of scar tissue developing between the conjunctiva and sclera. Because the success of glaucoma surgery is threatened by basic wound healing mechanisms, the operation frequently fails. Increasing the success rate requires the use of chemicals to suppress wound healing. However, serious complications often arise since some wound healing is required to prevent excessive flow though the hole. Complications associated with excessive flow of aqueous out of the eye include pathologically low intraocular pressure, infection, bleeding and swelling inside the eye. All of these complications can lead to acute and permanent blindness.

Research in improving glaucoma surgery has focused on the development of more effective inhibitors of wound healing. However, chemical suppression of wound healing is fundamentally flawed by the need to have some wound healing to protect the eye and yet not too much healing in order to keep the glaucoma drainage conduit patent. The major problem is that eyes differ greatly in their healing response and it is not possible to predict the extent of scar tissue formation before surgery. Therefore, it will never be possible to achieve just the right amount of wound healing inhibition in each patient. There always will be too many failures due to excessive scarring and too many complications such as ocular fluid leakage and pathologically low eye pressure due to inadequate healing.

A second approach to the surgical treatment of glaucoma involves the insertion of a bio-compatible tube into the anterior chamber. This type of device comprises the prior art relating to the present invention. The tube shunts aqueous to a reservoir or drainage body which is implanted on the surface of the sclera beneath the conjunctiva at the equator of the eye. Scar tissue inevitably develops around this reservoir to form a fibro-vascular capsule. These tube-shunt devices reduce eye pressure by a passive, pressure-dependent flow of aqueous humor across the capsular wall into the ocular tear film. The encapsulation surrounding the reservoir does not fully form for several days or even weeks after the surgical procedure. During this time period, the ocular pressure may be excessively low from excessive drainage of fluid through the open tube. Therefore, some of these devices include a valve system to impede flow and claim the ability to pre-set the pressure of this flow to a satisfactory level.

Although some type of valve restriction in outflow may be useful during the early period after surgery, the valve system becomes a detriment after the capsule has fully formed. When full encapsulation has been achieved, the flow of fluid out of the eye and regulation of ocular pressure are determined by a passive, pressure-dependent flow of fluid across the capsular wall. Therefore, this device will have a reduced capacity to lower eye pressure if a valve impedes outflow in addition to the encapsulation. These devices function best when free, bulk flow is allowed to occur along the conduit. This places as much fluid as possible internal to the encapsulated area and helps to promote the largest possible size of encapsulation as well as thinning of the encapsulation which improves flow across the capsule and conjunctiva.

A common characteristic of currently performed operations for glaucoma is the drainage of aqueous humor to a subconjunctival site. Whether the scleral fistula is created surgically or whether the fistula is maintained by an implanted tube, both operations drain this fluid to a subconjunctival site where it must pass across the scar tissue/capsule and continue through the conjunctiva. These operations fail when the scar tissue either closes the surgically-created opening or becomes so thick that the capsule does not permit adequate flow of fluid across the wall to permit successful reduction in ocular pressure. Therefore, like conventional glaucoma surgery, the tube-shunt operations also depend on the "right amount" of conjunctival and subconjunctival healing. As with other approaches to glaucoma surgery, the aqueous tube-shunts have not solved the extensive problems of unpredictable wound healing.

Thus, an object of the present invention is to avoid the problems associated with subconjunctival wound healing by providing a device that regulates pressure by allowing direct external drainage of ocular fluid. Normal wound healing would help to secure the device within the cornea but it could not obstruct the outflow of ocular fluid. Therefore, the usual mechanism of failure of glaucoma surgery would not apply to the present invention.

Prior Art

U.S. Pat. No. 3,788,327 issued Jan. 29, 1974 to Howard Donowitz, teaches a tubular shank member with a flange and valve means for controlling eye pressure. The tube is passed through the cornea with the flange portion protruding from the corneal surface. There are numerous potential problems with this design. Since the device is not flush with the corneal surface, it could cause abnormalities in the flow of tears over the ocular surface. This would cause dryness and possibly lead to areas of thinning and ulceration in the corneal tissue surrounding the flange. In addition, the portion of the cornea beneath the flange also would be highly susceptible to chronic dryness, thinning, and ulceration. The problems with ulceration may lead to infection and extrusion of the implant. The valve means taught by this patent also do not provide an effective barrier to infection. Bacteria and other pathogens could pass into the ocular fluid through this valve by osmosis even if the valve was successful in controlling the ocular pressure. This could cause internal ocular infection which usually leads to catastrophic visual loss. Despite this patent having issued in 1974, we are not aware of any clinical attempts to utilize this type of device.

U.S. Pat. No. 4,037,604 issued Jul. 26, 1977 to John B. Newkirk, teaches a plastic, tubular body with two open ends which is implanted in the eye wall and extends from the anterior chamber through the sclera into the subconjunctival space. Therefore, this patent teaches a subconjunctival drainage site and is subject to the problems of wound healing associated with drainage in this location. This device also contains a "unidirectional valve" which is counterproductive once the encapsulation around the device fully forms. This device was commercially available in the 1980's but is believed to be no longer in use due to the above-referenced problems.

U.S. Pat. No. 4,402,681 issued Sep. 6, 1983, to Joseph S. Haas, teaches a rigid implantation drainage device which is placed through the scleral tissues at the side of the eyeball. The tube appears to extend through the intact retina which can cause the potential serious complication of retinal detachment. In addition, the vitreous humor in the posterior segment of the eye would most likely obstruct this device if surgery was not performed to remove this material. Unfortunately, surgery to remove vitreous has a high complication rate. The placement of the drainage valve is not substantially flush with the ocular surface and therefore would likely cause serious irritation and possible erosion of the ocular surface.

U.S. Pat. No. 4,604,087 issued Aug. 5, 1986 to Neal H. Joseph, teaches a drainage tube implanted into the anterior chamber and extending to a drainage body which surrounds the eye at the equatorial position. This patent also teaches a subconjunctival drainage location. This device has been available commercially for many years. The absence of a valve mechanism has led to serious problems with excessively low intraocular pressure in the early period after surgery. The drainage body provokes the expected scar tissue encapsulation and the thickness of this capsule causes the operation to frequently fail.

U.S. Pat. No. 4,634,418, issued Jan. 6, 1987 to Perry S. Binder, teaches the use of a hydrogel material as a wick to help maintain a surgically-created opening in the scleral tissues. This patent also teaches a subconjunctival drainage location. The hydrogel implant is placed to maintain the scleral fistula. Unfortunately, this general type of glaucoma surgery fails most often because of the subconjunctival scar tissue formation rather than closure of the scleral fistula. Therefore, this patent does not address the basic problem of excessive subconjunctival scar tissue formation—the main cause of failure in glaucoma surgery.

U.S. Pat. No. 4,886,488, issued Dec. 12, 1989 issued to Thomas C. White, teaches a drainage device which conducts fluid from inside the anterior chamber along a tubular structure which leads into the nasal-lacrimal drainage system. There are several serious problems with this concept. The major problem is that the tube is placed within the nasal-lacrimal system which is generally colonized by pathologic bacteria. Although a micro-porous filter is taught in this patent, the risk of infection would still be unacceptable. Intraocular infection associated with this device could be catastrophic and lead to loss of all vision. In addition, the tube has an external location and would not be substantially flush with the ocular surface. This could lead to erosion of ocular tissue, irritation and infection.

U.S. Pat. No. 4,946,436 issued Aug. 7, 1990 to Stewart G. Smith, teaches a porous device for implantation in the sclera. This device attempts to avoid the problems of subconjunctival drainage of intraocular fluid. The intent of this device is to bypass the obstructed outflow system and reconnect the anterior chamber fluid with the natural outflow pathway which would lead to a normal ocular pressure. However, the placement of this device within the scleral tissues also would lead to scar tissue formation which could encapsulate the device and lead to an obstruction of drainage.

The porous material in the device is not intended by itself to regulate the flow of fluid but rather to reproduce the natural resistance to outflow existing in the eye's normal drain. This valve effect would be counterproductive in this concept just as it is a detriment in the patents which teach subconjunctival drainage. The scleral tissue surrounding the device would provide natural resistance to outflow and any further resistance intrinsic to the device would limit the ability of this device to reduce ocular pressure.

The concept of surgically removing the internal obstruction to outflow has been debated for decades and surgical attempts to achieve this have never been successful. It is not clear how this device would improve the ability of this surgical concept to reduce ocular pressure. The scleral tissue is not porous and it does not allow fluid to flow from the anterior chamber. The scleral channels that normally drain fluid from the eye into the bloodstream close permanently once glaucoma damage has occurred in the trabecular meshwork. It is therefore doubtful that this device could achieve any reduction in intraocular pressure.

U.S. Pat. No. 5,041,081, issued Aug. 10, 1991 and U.S. Pat. No. 5,127,901 issued Jul. 7, 1992, both to Ronald B. Oldrich, teach a trans-scleral conduit which drains fluid from the anterior chamber to a subconjunctival space. These devices could thus lead to subconjunctival scarring and encapsulation. The "one-way" flow-resisting valve would be counterproductive.

U.S. Pat. No. 5,073,163 issued Dec. 17, 1991, to Myron E. Lippman teaches a plastic block with multiple "through openings" to regulate flow from the anterior chamber though the device. This device also teaches subconjunctival drainage. The presence of the "through openings" to regulate pressure becomes unnecessary once the encapsulation has formed and ultimately reduces the ability of this device to lower intraocular pressure. This device has been available commercially for several years but has failed to reach a high level of success in its ability to reduce elevated eye pressure from glaucoma.

The devices described within the prior art have up to four separate components. First, they provide a tubular means for draining aqueous humor from the anterior chamber to a subscleral or subconjunctival site. Second, most have a valve mechanism for regulation of pressure and prevention of excessively low pressure after implantation. Third, some means is provided for securing the implant. Fourth, a few devices provide an infection barrier means.

The first two of these components relate to pressure reduction. The tubular means drains aqueous humor to the same subconjunctival site as conventional glaucoma surgery not involving implanted devices. A fibrovascular capsule inevitably forms around all implants and this limits drainage and causes a high rate of failure. Thus, the same mechanism of failure defeats all the drainage implant devices that defeats conventional glaucoma surgery. In addition, the valve further limits the bulk flow of fluid through the tubular means and this impedes the flow of aqueous across the capsule. These two problems are responsible for the high rate of failure that has been observed with the commercially-available drainage devices from the prior art. The success of these devices in stable positioning and preventing infection is irrelevant if adequate eye pressure control is not achieved.

SUMMARY OF THE INVENTION

The invention provides an implant in the cornea with a pressure-regulating conduit means allowing intraocular fluid to drain directly to the external ocular surface. External drainage eliminates the problem of encapsulation and scar tissue formation that renders the prior art ineffective for the treatment of glaucoma. The porous internal portion of the conduit provides the total pressure regulation of the device since no pressure-reducing encapsulation will occur around the device.

The device generally would have a rounded outer shaft or cylinder means with internal pores extending throughout the bore of the cylinder and close to the outer surface of the shaft wall. The two ends of the conduit are open to the flow of aqueous humor. The internal porous material provides for a pore size that regulates the intraocular pressure within an acceptable range. The eye is capable of extensive autoregulation in the adjustment of aqueous fluid production to achieve an acceptable intraocular pressure based on the existing outflow resistance. This device takes advantage of this mechanism and results in a normal intraocular pressure in situations where the prior art methods and devices and other conventional types of glaucoma surgery would be ineffective or technically impossible.

The present invention is substantially flush with the ocular surface. This eliminates the problems associated with any protuberance on the ocular surface as well as tissue erosion beneath any flange extending from an implant. The surface position of the implant allows the intraocular fluid to enter the tear film directly and not disturb the flow of tears over the ocular surface. Any protuberance on the ocular surface would cause a serious impairment in the flow of the tear film and could lead to localized areas of dryness and erosion in the cornea.

The device contains an infection barrier means provided by pores within the device which are small enough to prohibit the entrance of bacteria and other pathogens into the eye. Since the pressure always will be greater inside the eye as compared to the atmosphere, the flow of fluid always will be outward from the eye. This will help to prevent back-flow of fluid transporting bacteria into the eye. It is possible for the pore sizes within the device to be variable in size. For example, the pores on the surface of the device could be extremely small to provide the infection barrier means while the pores deeper within the shaft could be larger since they would be providing pressure-regulation instead of an infection barrier.

The outer shaft of the device may contain ridges or protuberances or other means for securing the device within the corneal stroma.

Various additional objects and advantages of the present invention will become apparent from the following detailed description, with reference to the accompanying drawings.

DETAILED DESCRIPTION OF THE PREFERRED INVENTION

Figure 1:
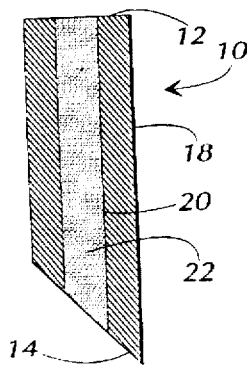
FIG. 1 is a cross sectional view of the present invention illustrating the shaft and core.
Figure 2:
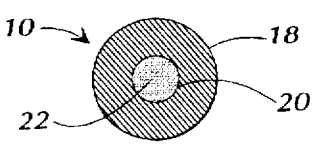
FIG. 2 is a top plan view of the invention.

In the first embodiment, the overall shape of the device 10 is substantially cylindrical as shown in FIG. 1. This is believed to be the most advantageous shape for the device; however, it is possible for other shapes, i.e. triangular, to be used providing they have the characteristics of the preferred embodiment. The proximal end 12, is substantially flat with the internal or distal end 14 sharpened to facilitate passage of the device through the cornea 16. The diameter of the conduit would be approximately 0.5 millimeters. The length of the conduit means or cylinder 18 to the sharpened end 14 would be approximately 0.8 to 1.2 millimeters.

The bore 20 of the elongated conduit is provided with a rigid porous flow control means or core 22 having numerous pores which permit adequate outward flow of aqueous to reduce intraocular pressure to a satisfactory level. By way of illustration, "normal" pressure is in the range of 10–15 mm/Hg while "abnormal" pressure can be in the range of 30–40 mm/Hg. However, the resistance to outflow would prevent pressure from falling to excessively low levels. The internal porosity could be achieved through various designs. In a preferred embodiment, the outer solid cylinder 18 contains a porous rigid material 22 affixed to its bore. Both of these elements can be made from metal, such as high-grade stainless steel, titanium, ceramics, or some other bio-compatible material. An advantageous material can be a sintered metal for both the conduit and the porous core. In general, the porous material and the outer shell are constructed from the same material. However, it is possible that different materials could be utilized in a single device. In an alternative construction, the desired pressure reduction could be achieved with a very small, single, hollow, channel running centrally through the substantially cylindrical device. The preferred embodiment also provides an infection barrier means. A thin porous layer on the surface of the device may contain extremely small pores, such as 0.2 microns in diameter, to prevent bacteria from gaining access to the conduit and entering the anterior chamber where they could cause intraocular infection. The infection barrier means could be a different material from the conduit and could be affixed to the conduit surface. The degree of thinness of the infection barrier layer would prevent it from protruding significantly beyond the ocular surface.

Figure 3:
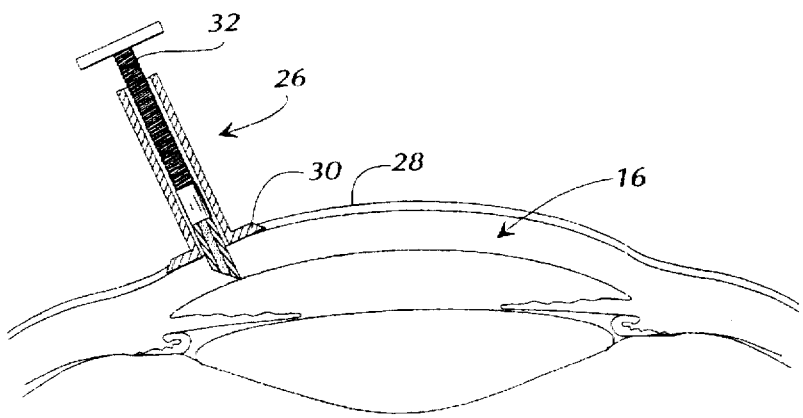
FIG. 3 is a side elevational view, shown partially in cross section, schematically illustrating the insertion of the present device in the cornea.

The device is implanted by placing it within a cranking mechanism 26 which adheres to the ocular surface 28 through a suction means 30, as shown in FIG. 3. The crank 32 of the insertion device acts to move the conduit through the corneal tissue 16 with the sharpened end passing into the anterior chamber 38. The insertion device positions the inserted conduit substantially flush with the ocular surface. No corneal tissue covers the device once it has been implanted. The device does not extend outwardly from its flattened proximal end and no flange or other protuberance is present.

Figure 4:
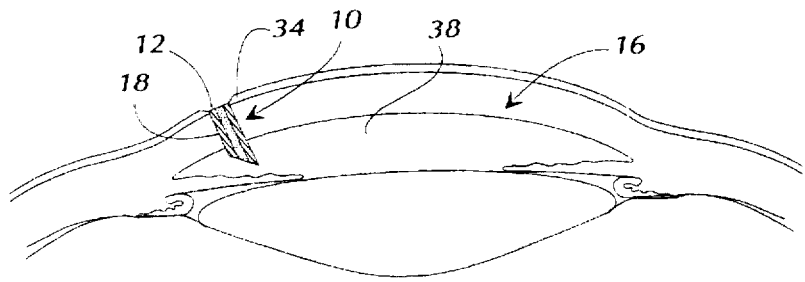
FIG. 4 is a schematic, partial cross-sectional view showing the present device in place in the eye.
Figure 5:
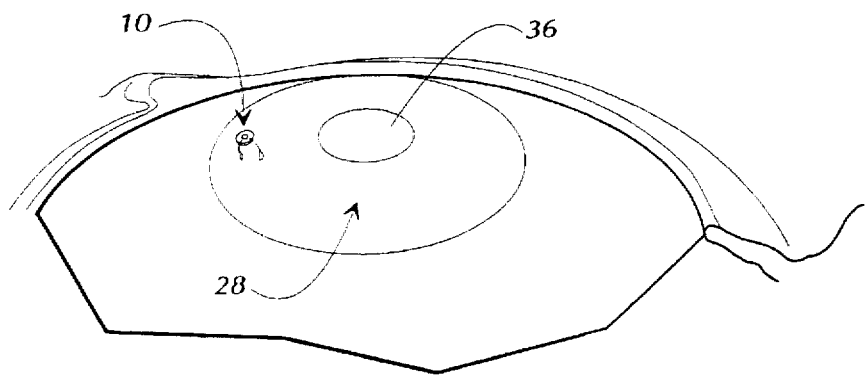
FIG. 5 is a partial perspective view schematically illustrating the drainage pattern of the device.

Proper placement of the device is shown in FIG. 4. The device is secured within the corneal stroma and extends from a position substantially flush with the ocular surface 28 into the anterior chamber. The pores within the conduit allow aqueous to pass through at an acceptable rate onto the ocular surface. This drainage allows the intraocular pressure to return to and be maintained at a normal level.

There are several other possible modifications of the surface of the outer shell which may improve the stability of the device within the corneal tissue. The outer surface of the cylinder could be provided with small indentations or protuberances (not shown) which would serve to further anchor the device within the cornea and prevent displacement.

In FIG. 3, it will be seen that the corneal epithelium 34 does not grow over the surface of the device so there is no chance for scar tissue to form and block egress of aqueous fluid. Furthermore, no portion of the device extends onto or over any portion of the ocular surface beyond the boundary of the device itself and therefore no erosion or damage can occur to corneal tissues such as that which can occur beneath flanges or other extensions taught by the prior art.

FIG. 4 shows a front view of the cornea with the device in place. The device is well removed from the pupil 36 and thus provides no obstruction to vision. The preferred placement of the device is 1 to 3 millimeters from the corneal limbus. Aqueous fluid from within the anterior chamber of the eye passes anteriorly through the conduit to the ocular surface where it mixes with the tear film. The fluid is then removed from the ocular surface along with other portions of the tear film into the lacrimal system as with any normal-functioning eye.

Thus, while an embodiment of a corneal pressure—relating implant device and modifications thereof have been shown and described in detail herein, various additional changes and modifications may be made without departing from the scope of the present invention.

We claim:

1. A unitary, pressure-regulating corneal implant device for use in controlling intraocular pressure of the cornea in an eye having a cornea, an ocular surface, a corneal stroma, and an anterior chamber; said corneal implant device comprising a conduit means having a bore with a porous core material disposed in said bore for allowing egress of aqueous humor from said anterior chamber of the eye to said ocular surface of the eye, said conduit means having a proximal end and a distal end, said proximal end being free of a surrounding flange and said distal end being sharpened so as to facilitate insertion of said device in the cornea, said conduit means being elongated for extending from a position substantially flush with the ocular surface of the eye through said corneal stroma, and into the anterior chamber.

2. A corneal implant device as defined in claim 1 in which, said proximal end is substantially flat so that said device can be positioned substantially flush with the ocular surface.

3. A corneal implant device as defined in claim 1 in which said core is permeable to fluids and impermeable to bacteria, and said core includes pores of varying diameters.

4. A corneal implant device as defined in claim 3 in which said proximal end has a substantially flat upper surface for positioning said upper surface substantially flush with the ocular surface of the eye.

5. A method for controlling the internal pressure of an eye comprising an anterior chamber containing aqueous humor, a cornea having an epithelium and an ocular surface, a corneal limbus, and a pupil, using a pressure-regulating corneal implant having a conduit means comprising a cylinder having a distal end, a proximal end and a bore therethrough having a porous core material disposed therein for allowing the egress of said aqueous humor from said anterior chamber to said ocular surface, said method comprising the steps of:

(a) removing the epithelium from the portion of the cornea through which said implant will be inserted; and (b) inserting said implant into the cornea such that the distal end thereof is disposed in the anterior chamber and the proximal end is disposed substantially flush with the ocular surface.

6. The method as defined in claim 5 and including the additional steps of placing said implant into an insertion device, utilizing said insertion device to access that portion of the cornea from which the epithelium has been removed; applying suction to the same portion of the cornea from which the epithelium has been removed; and, releasing the suction after said device has been inserted.

7. The method as defined in claim 5 in which said implant is inserted near the corneal limbus and away from the pupil.

8. A corneal implant for use in controlling intraocular pressure in a glaucomatous eye having a cornea with an ocular surface, and an anterior chamber containing aqueous humor, said implant comprising an elongated cylinder means having solid walls and a bore disposed therethrough, a porous flow control means disposed in said bore for permitting egress of aqueous humor from the anterior chamber of the eye, said implant having a proximal end and a distal end, said distal end being sharpened so as to facilitate insertion of said device in the cornea, and being disposed in the cornea with said proximal end being free of a surrounding flange and being located so as to be substantially flush with the ocular surface.

9. A corneal implant as defined in claim 8 in which said sharpened distal end is disposed in the anterior chamber of the eye after insertion through the cornea.

10. A corneal implant as defined in claim 9 in which said flow control means operates independently to conduct aqueous humor from the anterior chamber to the ocular surface when the pressure in the anterior chamber is above the normal range.

11. A corneal implant as defined in claim 8 in which said proximal end is substantially flat so as to not protrude above the ocular surface.

* * * * *